(12) United States Patent
Tsuchiya

(10) Patent No.: US 7,830,598 B2
(45) Date of Patent: Nov. 9, 2010

(54) MICROSCOPE STAGE AND MICROSCOPE OBSERVING UNIT

(75) Inventor: Hideharu Tsuchiya, Fujinomiya (JP)

(73) Assignee: TOKAI HIT Co., Ltd., Fujinomiya (JP)

( * ) Notice: Subject to any disclaimer, the term of this patent is extended or adjusted under 35 U.S.C. 154(b) by 396 days.

(21) Appl. No.: 11/990,024

(22) PCT Filed: Oct. 11, 2006

(86) PCT No.: PCT/JP2006/320274

§ 371 (c)(1),
(2), (4) Date: Feb. 5, 2008

(87) PCT Pub. No.: WO2007/043561

PCT Pub. Date: Apr. 19, 2007

(65) Prior Publication Data

US 2009/0141345 A1    Jun. 4, 2009

(30) Foreign Application Priority Data

Oct. 13, 2005  (JP) .............................. 2005-299412

(51) Int. Cl.
*G02B 21/26* (2006.01)
(52) U.S. Cl. .................. 359/395; 359/391; 359/393
(58) Field of Classification Search ................. 359/368, 359/391–398
See application file for complete search history.

(56) References Cited

U.S. PATENT DOCUMENTS 4,629,862 A * 12/1986 Kitagawa et al. ............ 219/200
5,181,382 A * 1/1993 Middlebrook ................ 62/3.2
5,343,018 A  8/1994 Limbach
2006/0092506 A1 * 5/2006 Tsuchiya et al. ............ 359/395

FOREIGN PATENT DOCUMENTS

| EP | 1 548 484 A1 | 6/2005 |
| JP | U-60-156996 | 10/1985 |
| JP | U-5-45624 | 6/1993 |
| JP | A-11-142749 | 5/1999 |
| JP | A-2000-214389 | 8/2000 |
| JP | A-2003-107364 | 4/2003 |

OTHER PUBLICATIONS

Extended European search report issued in European Patent Application No. 06811581.5 issued on Dec. 28, 2009.

* cited by examiner

*Primary Examiner*—Thong Nguyen
(74) *Attorney, Agent, or Firm*—Oliff & Berridge, PLC

(57) ABSTRACT

A microscope stage capable of always heating the entire culture vessel even when the culture vessel is moved in two-dimensional directions, and allowing an object lens and a condenser even in a high-power microscope to approach an object of observation such as a cell until they come into focus. A heating unit (58) faces a well plate (37) on a drive base (49) even when the drive base (49) is driven to any position in two-dimensional directions. Therefore, all the cells A in the small compartments (45) of the well plate (37) are always heated. Since the microscope stage (25) is constituted such that a lower-side base (71) houses an upper-side base (73) and a fixed base (47) in recessed portions, its thickness is considerably small. Accordingly, an object lens (5) and a condenser (3) can approach close to the cells A. Therefore, it is possible for high-power object lens (5) and condenser (3) to focus on the cells A.

13 Claims, 19 Drawing Sheets

(a)

(b)

(a)

(b)

MICROSCOPE STAGE AND MICROSCOPE OBSERVING UNIT

BACKGROUND

The present invention relates generally to a microscope stage capable of heating an entire culture vessel containing specimen such as cells or microorganism to be observed, and a microscope observing unit including the microscope stage and a culture device to be disposed on the stage.

It has been well known in the art to use shallow cylindrical dishes of a diameter of 35 mm as culture vessels for cells or microorganisms. Recently, there have been used culture vessels so called well plates having a number of cells or compartment, each well cells Accommodating a culture solution and cells or microorganisms. The typical dimension of the well plates is of a width of 85 mm and a length of 115 mm. Namely, the well plates are substantially larger than the dishes. The well plates have a variety of depths. As can be seen from above, there has been used culture vessels of various sizes in dependence upon their applications.

When it is intended to culture cells or microorganisms, it is required to keep a given temperature within the dishes or well plates, for example, at 37° C. It is further required to control atmosphere within the dishes or well plates in terms of $CO_2$ concentration, the humidity and the like.

Generally, light microscopes are used for observation of cells and the like. When observing growing cells or microorganisms, it is required to heat a culture vessel accommodating the cells therein disposed on the microscope stage. In order to accomplish the heating of the vessel, commercially available is stage heaters adapted to be fit into the opening formed in the central portion of the microscope stage. Each stage heater includes a glass plate on which an electrically conductive transparent film applied. Upon energized, the film generates heat energy to heat the culture vessel disposed thereon.

However, especially for a well plate of larger size, the entire well plate is not heated by the commercial stage heaters, i.e. at least a portion of the well plate is not heated. This is because the stage heater as mentioned above is positioned only on the central portion of the microscope stage. Thus, a portion of the cells or microorganisms can not be disposed oppositely with the stage heater.

Further, for well plates, observation is done for each well cells Accommodating cell or microorganisms and culture solution. In this connection, it is required to displace the well plate repeatedly in order to align one well cell to be observed with the optical axis of the microscope objective lens by the cell number. It is cumbersome to displace the well plate manually. Further, it is difficult to displace the well plate precisely by hands. In this connection, it is requested to use a microscope stage of such a type that the base member, on which a culture vessel is disposed, can be shifted in two dimensional directions.

However, the two dimensionally movable microscope stage of this kind is relatively thick, since it is of a three-stage structure including a fixed base to be secured on the microscope, a lower base adapted to be movable in side to side direction (referred hereinafter to as x-direction), and an upper base adapted to be movable in back and force direction (referred hereinafter to as y-direction). If the stage heater of the type above mentioned is simply incorporated into the movable type microscope stage, the overall thickness of the microscope stage will further thicken. Thus, the distance between specimen in each well cell of a well plate disposed on the microscope stage and the objective lens is further increased in addition of the thickness of the stage heater. In this connection, it will be difficult or impossible to focus the objective lens on the specimen in each well cell, if as the microscope is a high-powered one. In other words, it will be difficult or impossible to focus the objective lens on specimen such as cells or microorganisms to be observed even if the objective lens is approached to its closet limit of the up-down or vertical direction (referred hereinafter to as z-direction). This is because the displace-able range of the objective lens in vertical direction is already be determined and limited on the basis of the microscope stage of a simple one-stage structure. Therefore, if the stage heater of the type above mentioned is simply incorporated into the movable type microscope stage, the objective lens can not be focused on specimen even under the approach-able limit.

Further, the condenser is also displaced relatively away from specimen to be observed because of the thickness of the movable type, three-stage microscope stage. In this connection, it will be difficult or impossible to focus light on the specimen to be observed, and, thus, sufficient amount of light may not be projected thereon.

In other words, the thickness of the movable microscope stage becomes large, the objective lens as well as the condenser is not approachable sufficiently to the specimen can, so that the objective lens as well as the condenser can not be bring closer to the specimen sufficiently to focus thereon.

It is an object of the present invention is to provide a microscope stage capable of always heating entire culture vessels such as well plates of various shapes or sizes, and capable of bringing the objective lens as well as the condenser closer to the specimen to be observed sufficiently to focus thereon even when the microscope is a high powered one. Further, it is another object of the present invention is to provide a microscope observing unit forming an enclosed space in combination with the drive base of the microscope stage, and capable of controlling atmosphere in temperature and/or humidity within the enclosed space.

SUMMARY

In accordance with the invention defined as a first aspect, there is provided a microscope stage comprising: a fixed base, a movable base on which a culture vessel accommodating an object to be observed is disposable, the movable base being movable relative to the fixed base in two-dimensional directions within a plane extending perpendicular to an optical axis of an objective lens, a shift means for shifting the movable base in two-dimensional directions, a light-transmittable portion for passing light, formed through the movable base with a size corresponding to an object-accommodating portion in the culture vessel, a stage heater provided on the fixed base for heating the entire culture vessel regardless of the two-dimensional displacement of the movable base, and a light-transmittable, circular portion of the stage heater for passing the light therethrough for making observation through the objective lens.

In accordance with the invention defined as a second aspect, there is provided the microscope stage according to the first aspect, wherein the circular portion of the stage heater for passing the light is provided opposite to a condenser of the microscope.

In accordance with the invention defined as a third aspect, there is provided the microscope stage according to the first or second aspect, wherein the light-transmittable portion of the movable base is an opening.

In accordance with the invention defined as a fourth aspect, there is provided the microscope stage according to the third aspect, wherein the size of an opening of the movable base corresponds to a two-dimensional maximum size of the culture vessel.

In accordance with the invention defined as a fifth aspect, there is provided the microscope stage according to the fourth aspect, further comprising an adapter adaptable within the opening of the movable base, the adapter being formed with an opening of a size corresponding to another small culture vessel.

In accordance with the invention defined as a sixth aspect, there is provided the microscope stage according to the fifth aspect, wherein the movable base includes a fixing means for securing the culture vessel of maximum size or the adapter in the opening of the movable base.

In accordance with the invention defined as a seventh aspect, there is provided the microscope stage according to any one of the first to sixth aspects, wherein the light transmittable, circular portion of the stage heater is a through hole.

In accordance with the invention defined as a eighth aspect, there is provided the microscope stage according to any one of the first to sixth aspects, wherein a heating section of the stage heater includes a transparent base plate and an electrically conductive transparent film.

In accordance with the invention defined as a ninth aspect, there is provided the microscope stage according to any one of the first to eighth aspects, wherein the movable base includes a lower base and an upper base, the lower base is linearly movable relative to the fixed base in a first direction, and the upper base is linearly movable relative to the lower base in a second direction perpendicular to the first direction.

In accordance with the invention defined as a tenth aspect, there is provided the microscope stage according to the ninth aspect, wherein the upper surface of the lower base is recessed to receive the upper base, and the lower surface of the lower base is recessed to receive the fixed base.

In accordance with the invention defined as a eleventh aspect, there is provided a microscope observing unit including; the microscope stage according to any one of the first to tenth aspects, a culture device disposed on the movable base to form an enclosed space in combination with the movable base, provided with a means for controlling the atmosphere of the enclosed space in temperature and humidity.

In accordance with the invention defined as a 12th aspect, there is provided the microscope observing unit according to the eleventh aspect, the culture device comprising: a housing adapted to be disposed on the movable base, and a top heater adapted to be disposed on the housing, wherein the top heater is provided with a heat producing portion covering over an upper opening of a housing, with a transparent base plate and an electrically conductive transparent film formed thereon.

In accordance with the invention defined as a 13th aspect, there is provided the microscope observing unit according to the 12th aspect, further comprising a spacer frame adapted to be interposed between the top heater and the housing for providing an additional height to the enclosed space in correspondence to the height of the culture vessel being used.

The microscope stage of the present invention is applicable to culture vessels, including well plates, of various shapes or sizes. The microscope stage of the present invention is capable of always heating the entire culture vessel.

The microscope stage has a structure capable of shifting the culture vessel disposed thereon in two-dimensional directions. The objective lens as well as the condenser can be brought closer to an object to be observed sufficiently to focus thereon even when the objective lens is one of high magnifying power.

Further, the microscope observing unit is capable of forming an enclosed space in combination with a movable base of the microscope stage, and capable of controlling the atmosphere within the enclosed space in temperature and/or humidity.

BRIEF DESCRIPTION OF THE DRAWINGS

Embodiments of the present invention will now be described more fully with reference to accompanying drawings in which.

DETAILED DESCRIPTION OF EMBODIMENTS

Figure 1:
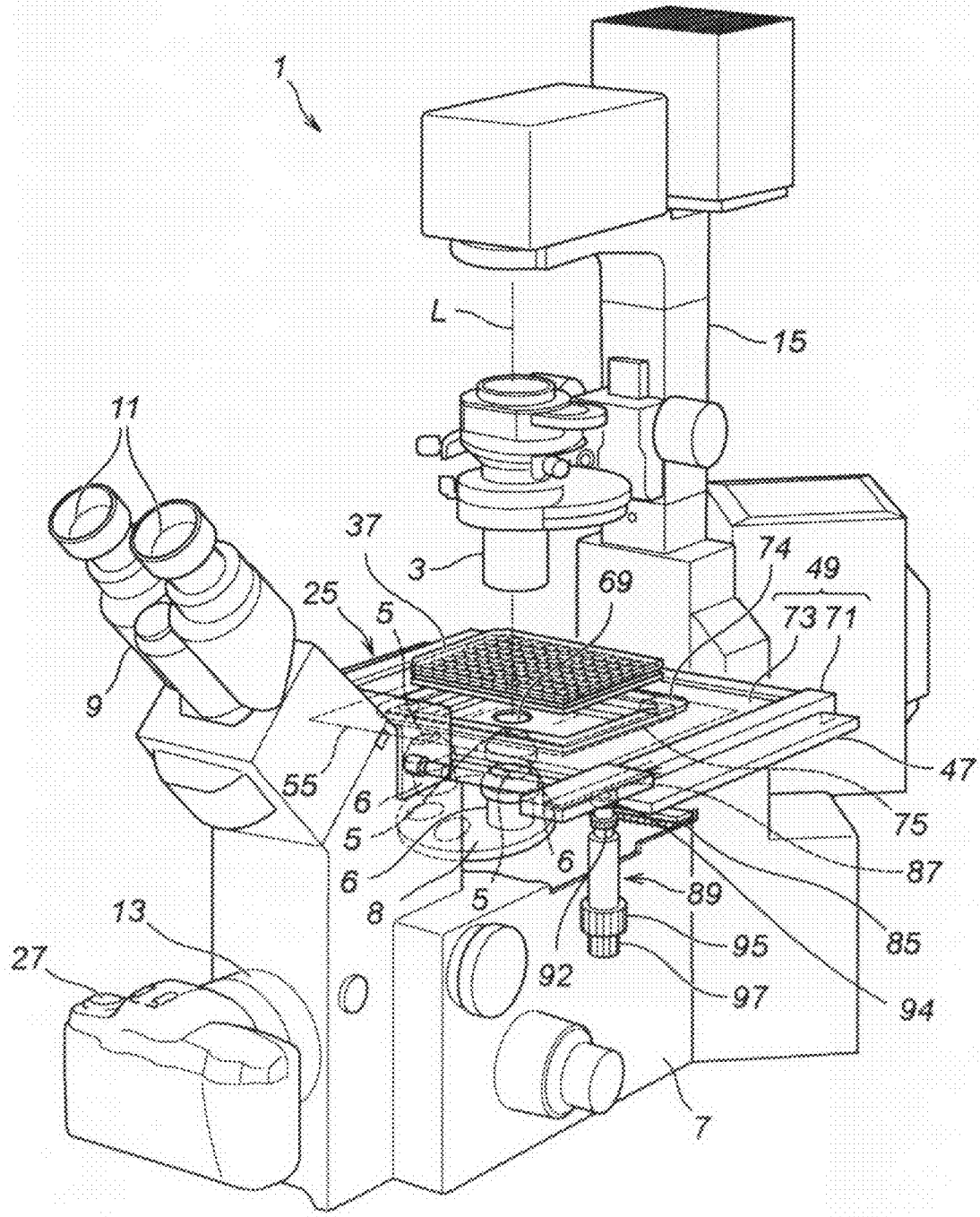
FIG. 1 is a perspective view illustrating a microscope to which the present invention is to be equipped.

A best embodiment of a microscope observing unit including a microscope stage according to the present invention will now be described with reference to the attached drawings.

In the following description, a microscope to which the embodiment of the present invention is to be applied is described in summary, and then vessels for accommodating an object to be observed is described. The microscope stage and the microscope observing unit including the stage will then be described concretely.

A microscope 1 is provided with a microscope stage 25 of the present invention. Objectives 5 are attached to the end of body tubes 6 and disposed under the stage 25. The three body tubes 6 and the objectives 5 attached thereto different in their magnifying power are supported by a revolving piece 8.

The microscope 1 further includes binocular tubes 9, eye pieces 11 attached to the tubes 9, and a camera port 13 provided through a front, lower part of a body 7.

Further, a penetrating illumination column 15 is provided on a rear, upper part of the body 7. The column 15 supports a condenser 3 above the stage 25.

As can be seen from the attached drawings, a microscope observing unit 31 according to the embodiment comprise the microscope stage 25 and a culture device 29 adapted to be disposed on the stage 25.

Culture vessels of various configuration are illustrated in FIGS. 2(a)–2(d).

Figure 2:
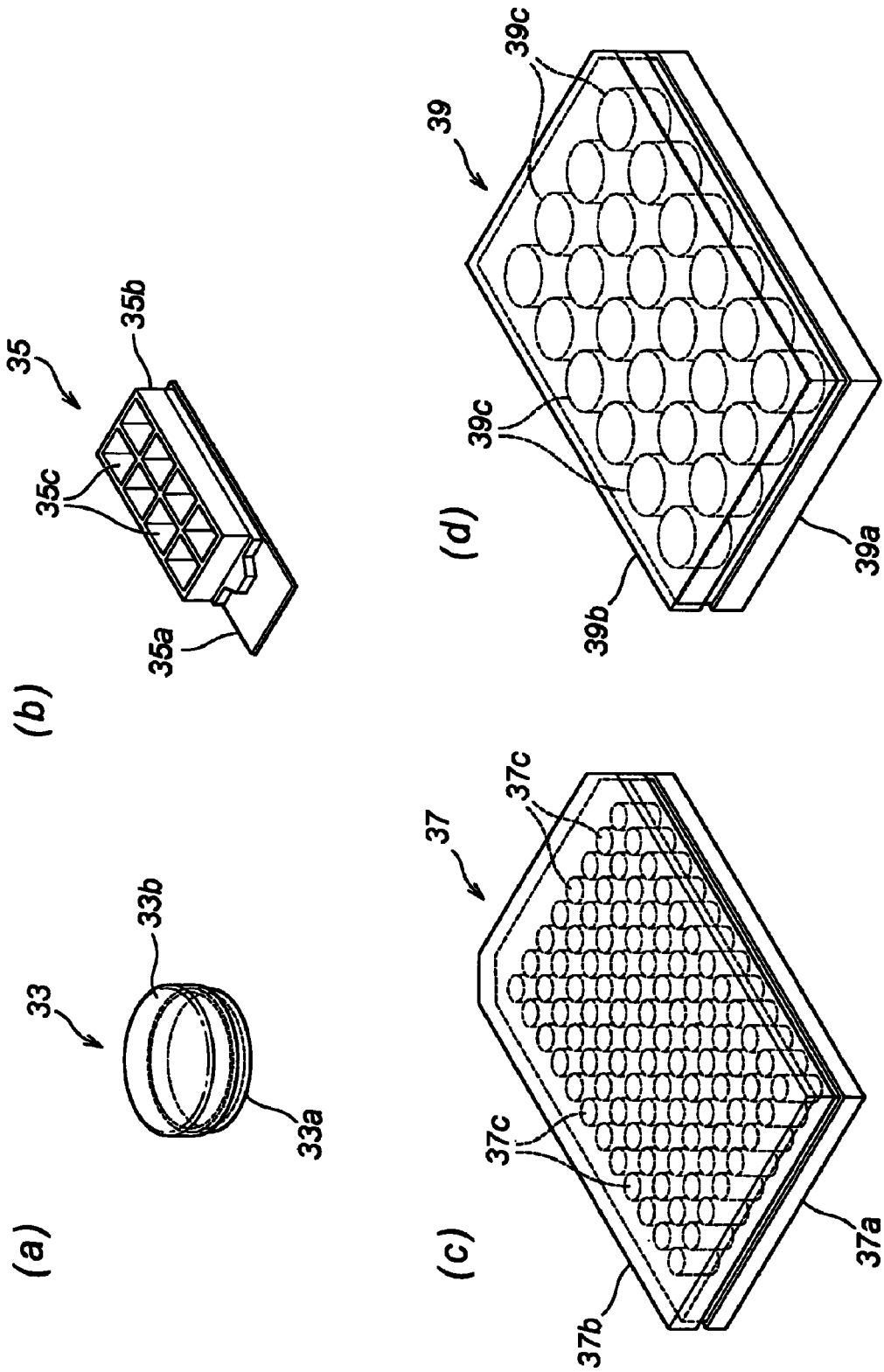
FIG. 2(a)-(d) are perspective views illustrating various kinds of culture vessels for accommodating objects to be observed.

A dish 33 shown in FIG. 2(a) is of transparent plastic material. The dish includes a shallow cylindrical body 33a and a lid 33b for covering the body 33a. The diameter of the body 33a is about 35 mm, and the depth is about 10 mm. The dish is adapted to accommodate as one specimen cells and the like.

A well plate 35 shown in FIG. 2(b) comprises a slide glass 35a and a frame member 35b. The slide glass 35a has a width of about 75 mm, a length of about 25 mm, and a thickness of about 1 mm. The frame member 35b has a width of about 10 mm, a length of about 8 mm, and a depth of about 11.5 mm. The frame member 35b makes eight compartments 35c for accommodating specimens such as cells.

A well plate 37 shown in FIG. 2(c) is of transparent plastic material, and includes a body 37a and a lid 37b. The body 37a is a shallow container. The body 37a has a plurality of cylindrical compartments 37c, each compartment 37c having a diameter of about 6.5 mm, and a depth of about 10.5 mm. In the body 37a, the compartments 37c are aligned in 12 in the width direction and 8 in the longitudinal direction so that the total number of the compartments 37c is 96. The opened upper surface of the body 37a is adapted to be covered with the lid 37b. The well plate 37 has, in the outer size, a width of about 127 mm, a length of about 85 mm, and the height of about 16 mm.

A well plate 39 shown in FIG. 2(d) is of transparent plastic material, and includes a body 39a and a lid 39b. The body 39a includes a plurality of cylindrical compartments 39c. Each compartment 39c has a diameter of about 16 mm, and a depth of about 17 mm. In the body 39a, the compartments 39c are aligned in 6 in the width direction and 4 in the longitudinal direction so that the total number of the compartments 39c is 24. The opened upper surface of the body 39a is adapted to be covered with the lid 39a. The well plate 39 has, in the outer size, a width of about 127 mm, a length of about 85 mm, and the height of about 22.5 mm.

In the illustrated embodiments, the well plates 37 and 39 as shown in FIGS. 2(c) and 2(d) is a largest in the two-directions, and used one culture vessel. The dish 33 and the well plate 35 are used as other culture vessels on the stage with adapters 99A and 99B as mentioned herein below. The height of the well plate 39 is a largest among the culture vessels.

The microscope stage 25 will now be described in detail.

Figure 3:
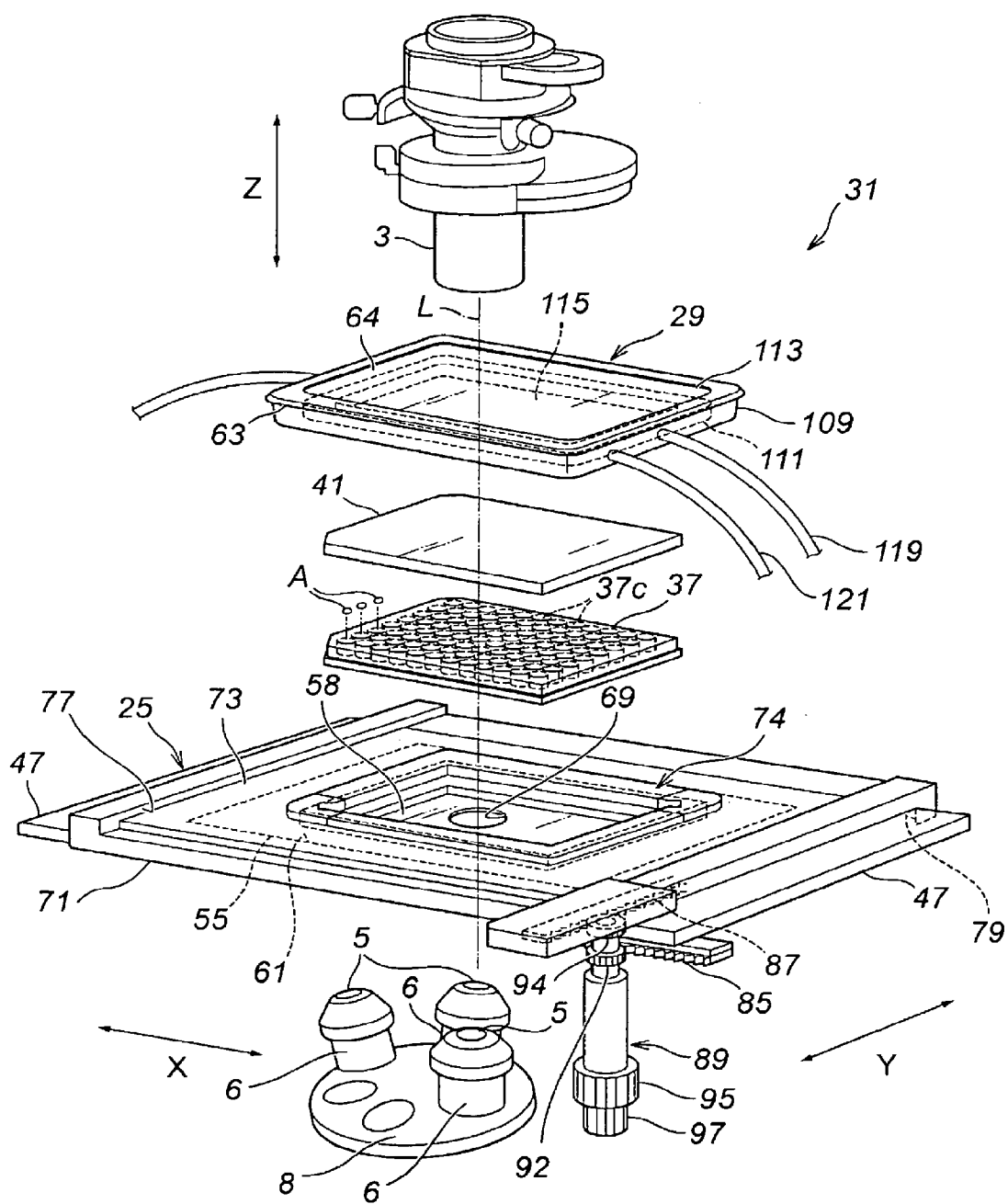
FIG. 3 is an exploded perspective view illustrating a microscope observing unit as an embodiment of the present invention, including a microscope stage and a culture device set on the stage.
Figure 4:
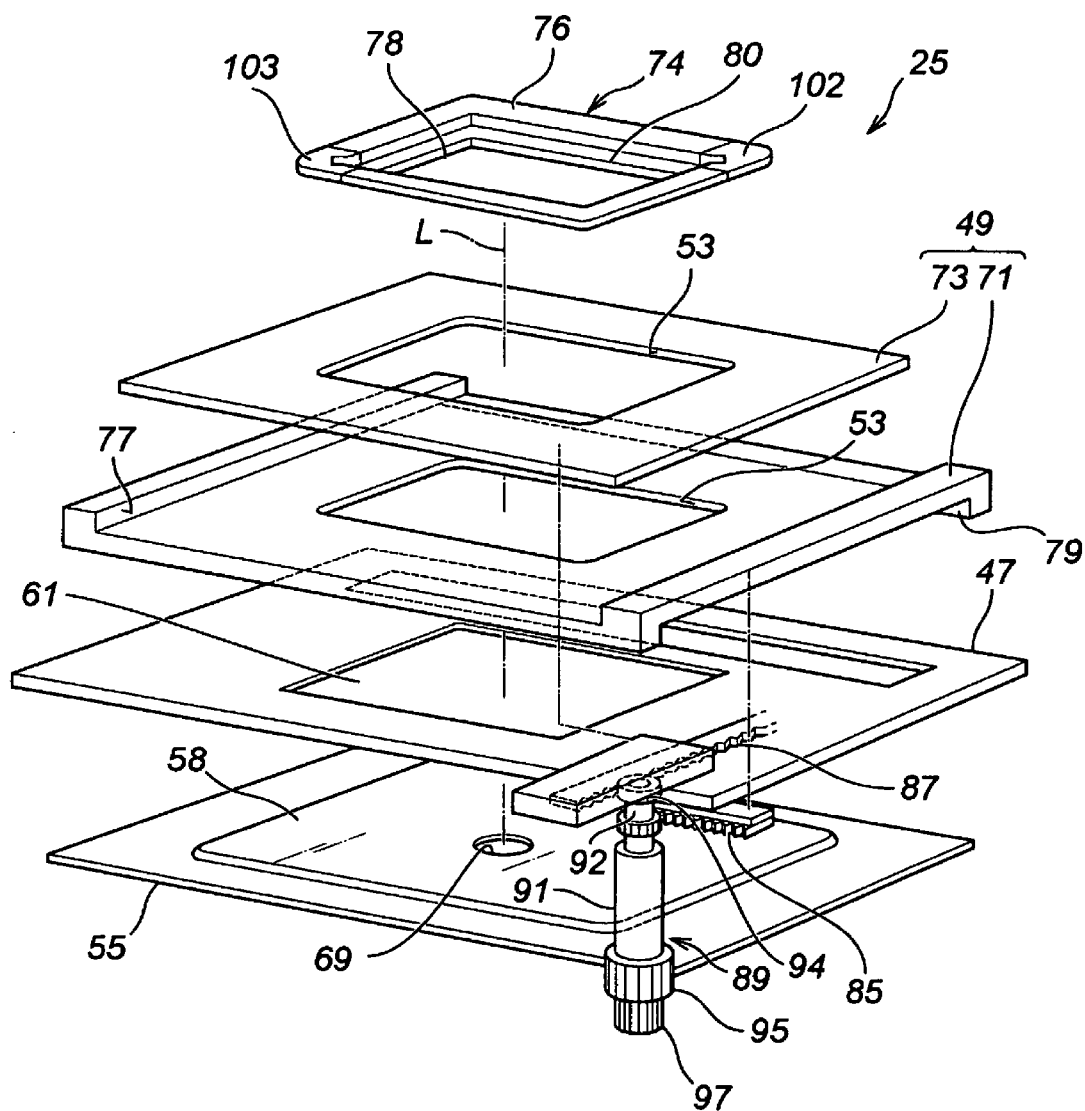
FIG. 4 is an exploded perspective view illustrating the microscope stage as the embodiment.

As shown in FIGS. 3 and 4, the microscope stage 25 includes a fixed base 47, a movable base 49 which is adapted shift-ably in two-directions within a plane perpendicular to the optical axis of the objective 5, a driving means for shifting the movable base 49 in two-directions, an opening 53 formed through the movable base 49, and a stage heater 55 adapted to be mounted on the lower surface of the fixed base 47.

The arrangement of the fixed base 47 and the stage heater 55 will now be described in detail.

The fixed base 47 may be a rectangular plate member through which a rectangular window 61 is provided for transmitting light therethrough. The stage heater 55 includes a rectangular heating section 58 containing heating wire (not shown) adapted to convert electricity to heat energy. The heating section 58 is protruding slightly upward. The heating section 58 is also provided with a circular opening 69 for transmitting light therethrough. The opening 69 is adapted to be positioned between and in opposite to the objective 5 and the condenser 3.

The fixed base 47 is recessed on the lower surface thereof for accommodating the heating section 58. The stage heater 55 is mounted on the lower surface of the fixed base 47 whereby the heating section 58 is adapted to the lower surface of the fixed base 47. The central portion of the heating section 58 is exposed through the window 61. The size and the shape of the heating section 58 is, as mentioned herein below, determined to cover the displacement range of the well plates 37 and 39 on the movable base 49, so that the well plates 37 and 39 are always being heated nevertheless displacement of the movable base 49 on the stage 25.

The arrangement of the movable base 49 will now be described in detail.

The movable base 49 includes a lower base 71 and an upper base 73. The lower base 71 is provided with an upper surface recess 77 in which the upper base 73 is received. The lower base 71 is provided with a lower surface recess 79 in which the fixed base 47 is received. Therefore, this arrangement results in reduction substantially in the total thickness of the stage 25 relative to that of the existing movable stage.

Figure 5:
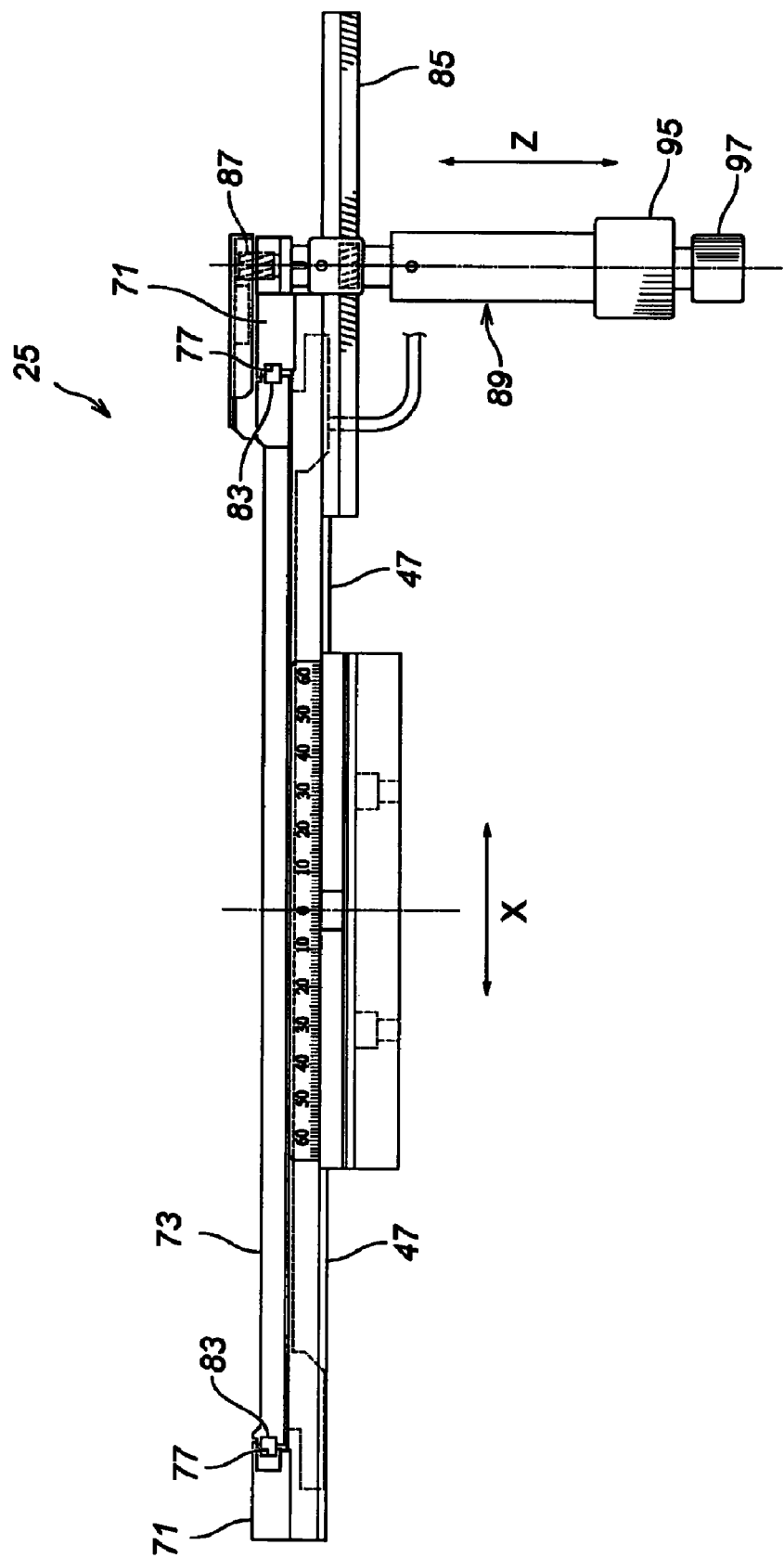
FIG. 5 is a front view illustrating the microscope stage of FIG. 4.
Figure 6:
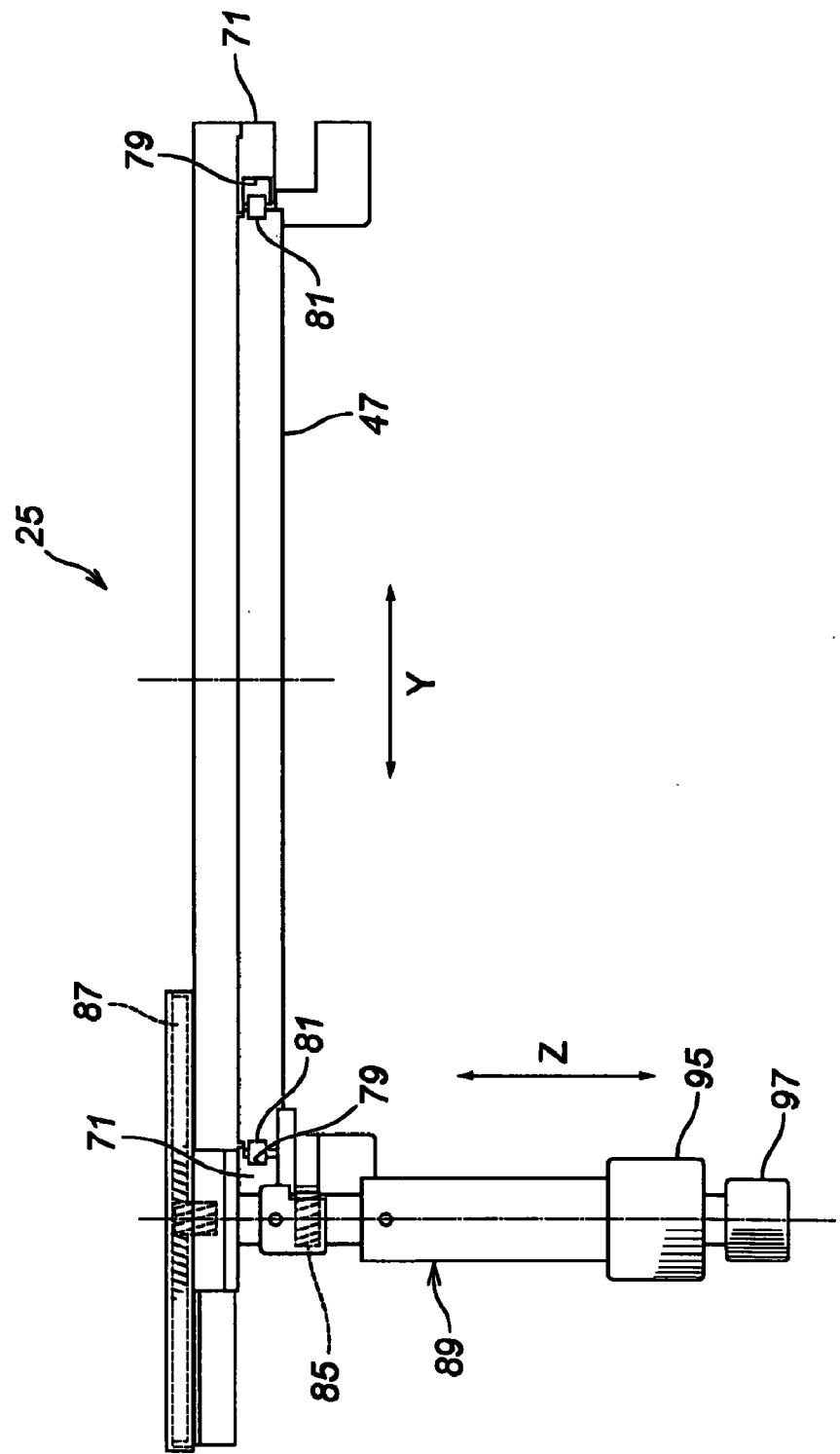
FIG. 6 is a side view illustrating the microscope stage of FIG. 4.
Figure 7:
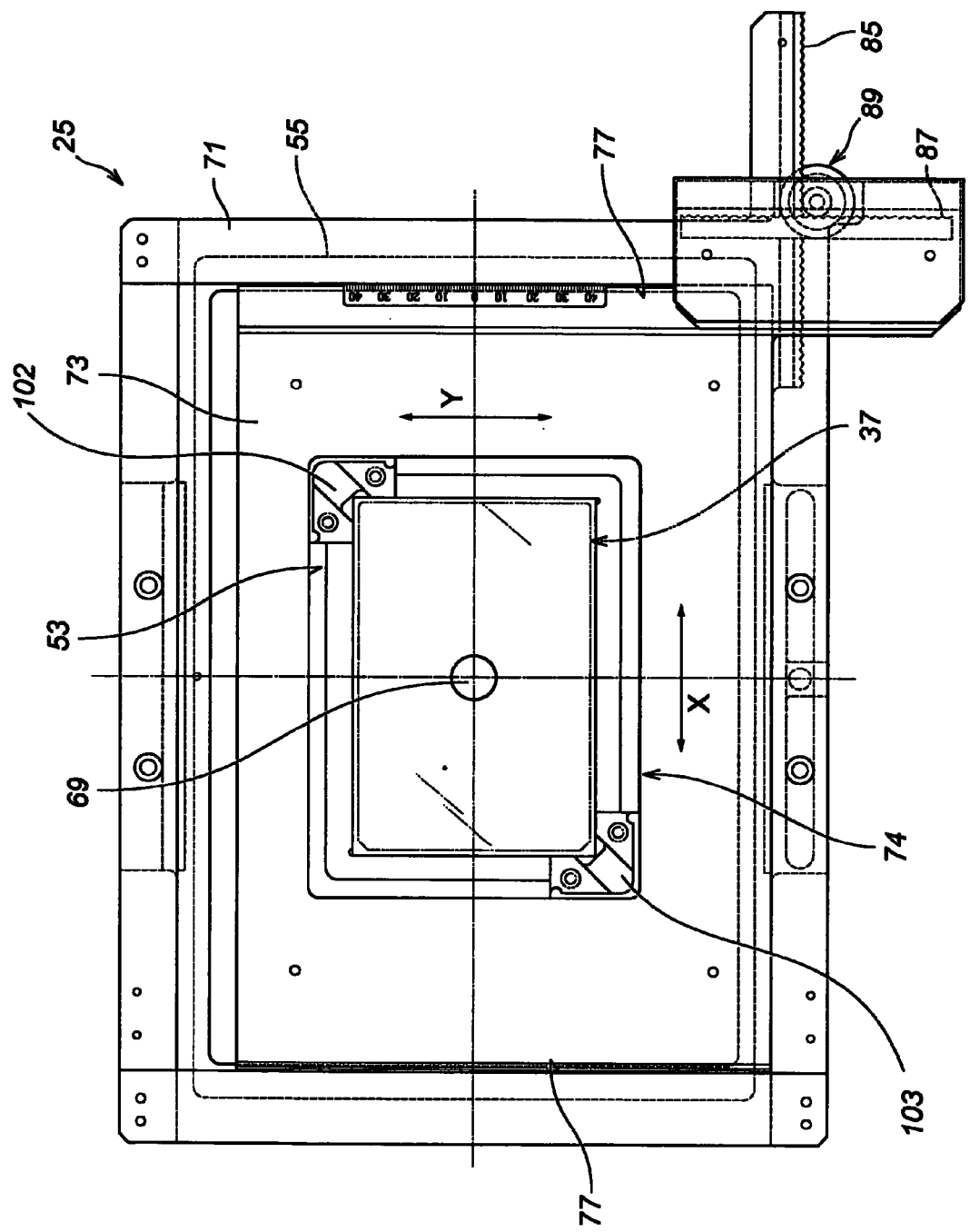
FIG. 7 is a plan view illustrating the microscope stage of FIG. 4.

As can be seen in FIG. 6, the lower base 71 is attached to the fixed base 47 via linear guide members 81, so that the lower base 71 can shift linearly side to side direction (referred hereinafter to as x-direction). Further, as can be seen in FIG. 5, the upper base 73 is attached to the lower base 71 via linear guide members 83, so that the upper base 73 can shift linearly back and force direction (referred hereinafter to as y-direction) in generally perpendicular to the x-direction.

The lower base 71 and the upper base 73 also have rectangular openings 53 for transmitting light therethrough.

The lower base 71 is provided on its lower surface with a rack 85, and the upper base 73 is also provided on its lower surface with a rack 87.

The upper base 73 is provided with a pinion mechanism 89 including pinions 92 and 94. The pinion 92 is adapted to mesh with the rack 85 of the lower base 71, and the pinion 94 is adapted to mesh with the rack 87 of the upper base 73. Rotating a control knob 95 rotates the pinion 92, and rotating a control knob 97 will rotate the pinion 94. Thus, the pinion mechanism 89 and the racks 85 and 87 establish a driving means for shifting the movable base 49 in the two directions.

The movable base 49 further includes a vessel-keeping frame 74 for holding a vessel. The vessel-keeping frame 74 is adapted to be mounted in the opening 53. The arrangement of the vessel-keeping frame 74 will now be described in detail.

A reference numeral 76 denotes a frame member having a rectangular opening 78 for transmitting light therethrough. As mentioned herein below, the opening 78 is of a size to accommodate all of the 96 compartments 37c when fitting the well plate 37 into the opening 78. The opening 78 is also of a size to accommodate all of the 24 compartments 39c when fitting the well plate 39 into the opening 78. An inwardly extending shelf-shaped portion 80 is formed in the lower end of the inner peripheral surface of the opening 78 of the frame member 76.

At one of the corners of the frame member 76 is provided with a frame fixing means 135 comprising a corner block 103, a coil spring 141 accommodated within the corner block 103, a tongue 137 substantial part of which is accommodated within the corner block 103, the remaining part protruding outwardly from the corner block 103, and a detent (not shown) for preventing the tongue 137 from falling off from the corner block 103. The tongue 137 is being urged by the coil spring 141 to protrude outwardly from the corner block 103.

At the inner side of the corner block 103 is formed a cutout 104.

At the corner opposite to that having the frame fixing means 135 is provide with a fixing means 101 for securing the well plate 37 or 39 comprising a corner block 102, a coil spring 106 accommodated within the corner block 102, a tongue 105 substantial part of which is accommodated within the corner block 102, the remaining part protruding outwardly from the corner block 102, and a detent (not shown) for preventing the tongue 105 from falling off from the corner block 102. The tongue 105 is being urged by the coil spring 106 to protrude outwardly from the corner block 102. At the tip of the tongue 105 is formed a recess 105a.

At the inner side of the corner block 102 is formed a cutout 107. The tip of the tongue 105 protrudes from the cutout 107.

The well plate fixing means 101 are also used as a means for fixing the adapters 99A, 99B as mentioned herein below.

The microscope observing unit 31 is accomplished by setting a culture device 29 on the microscope stage 25.

The culture device 29 will now be described in detail.

Figure 8:
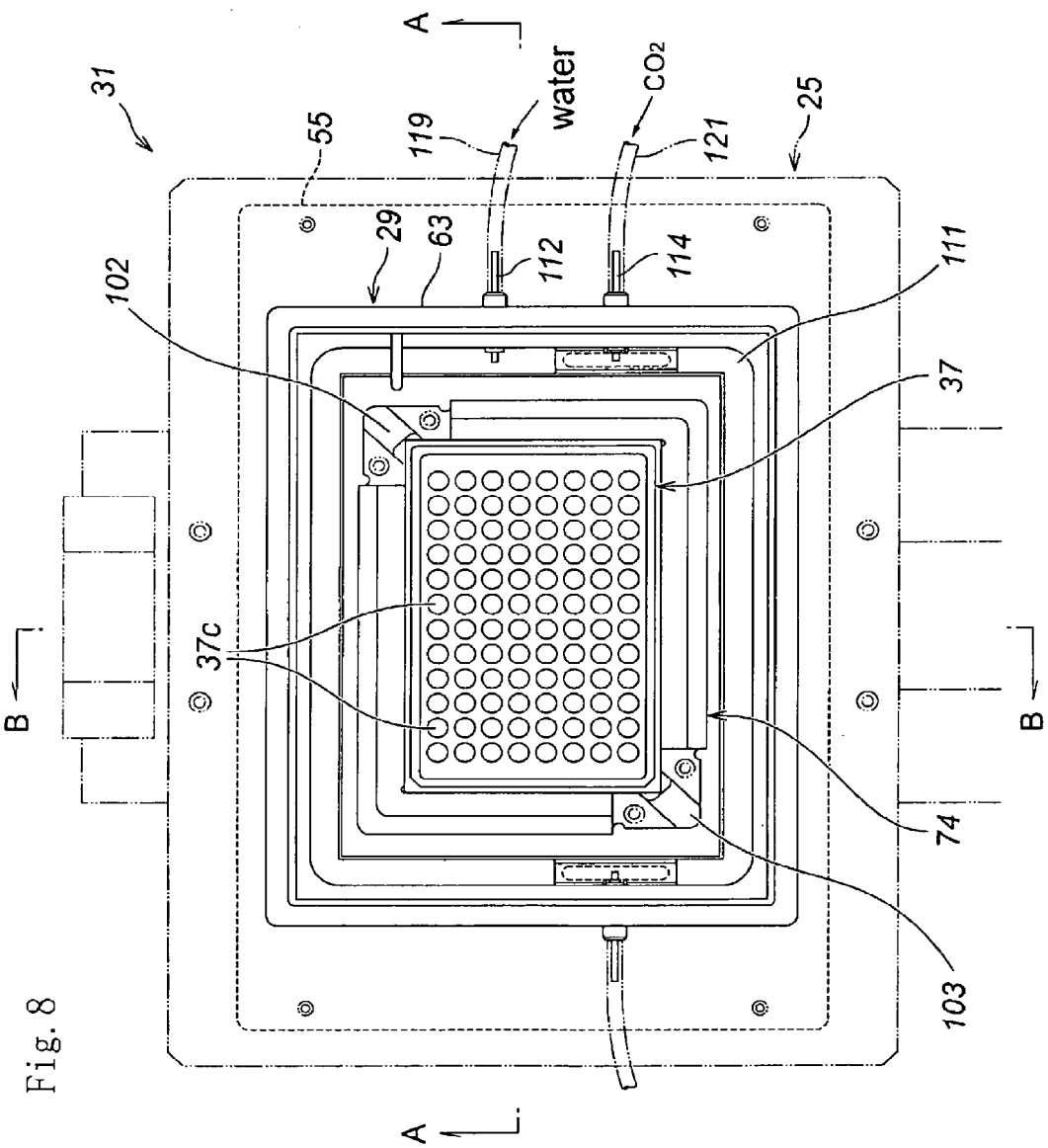
FIG. 8 is a plan view illustrating the microscope observing unit in which a culture device is disposed on the microscope stage of FIG. 4.

A reference numeral 109 denotes a housing in frame form. On the upper surface of the housing 109 is formed with a recess 109a. A water tank 111 is also provided within the housing 109. As can be seen from FIG. 8, the housing 109 is further provided with a water supplying tube 112. The one end of the water supplying tube 112 is protruding into the water tank 111 and the other end of which is protruding outwardly from the outer surface of the housing 109 and connected to a water supplying conduit 119. The housing 109 is also provided with a gas supplying tube 114. The one end of the gas supplying tube 114 is protruding into the water tank 111 and the other end of which is protruding outwardly from the outer surface of the housing 109 and connected to a gas supplying conduit 121.

A reference numeral 113 denotes a top heater to be placed on the housing 109. The top heater 113 includes a supporting frame 63 and a transparent heater 64 formed by bonding a pair of glass plates by means of silicone resin. One glass plate is a base plate. On the other plate is formed a layer of electrically conductive transparent film. The top heater 113 can produce heat energy by supplying electric energy to the transparent film and converting electric energy to the heat energy.

A means for controlling the atmosphere in temperature and/or humidity of an enclosed space 115 includes the stage heater 55, the top heater 113, the gas supplying tube 114, the gas supplying conduit 121, the water supplying tube 112, the water supplying conduit 119, and a temperature sensor (not shown).

Figure 15:
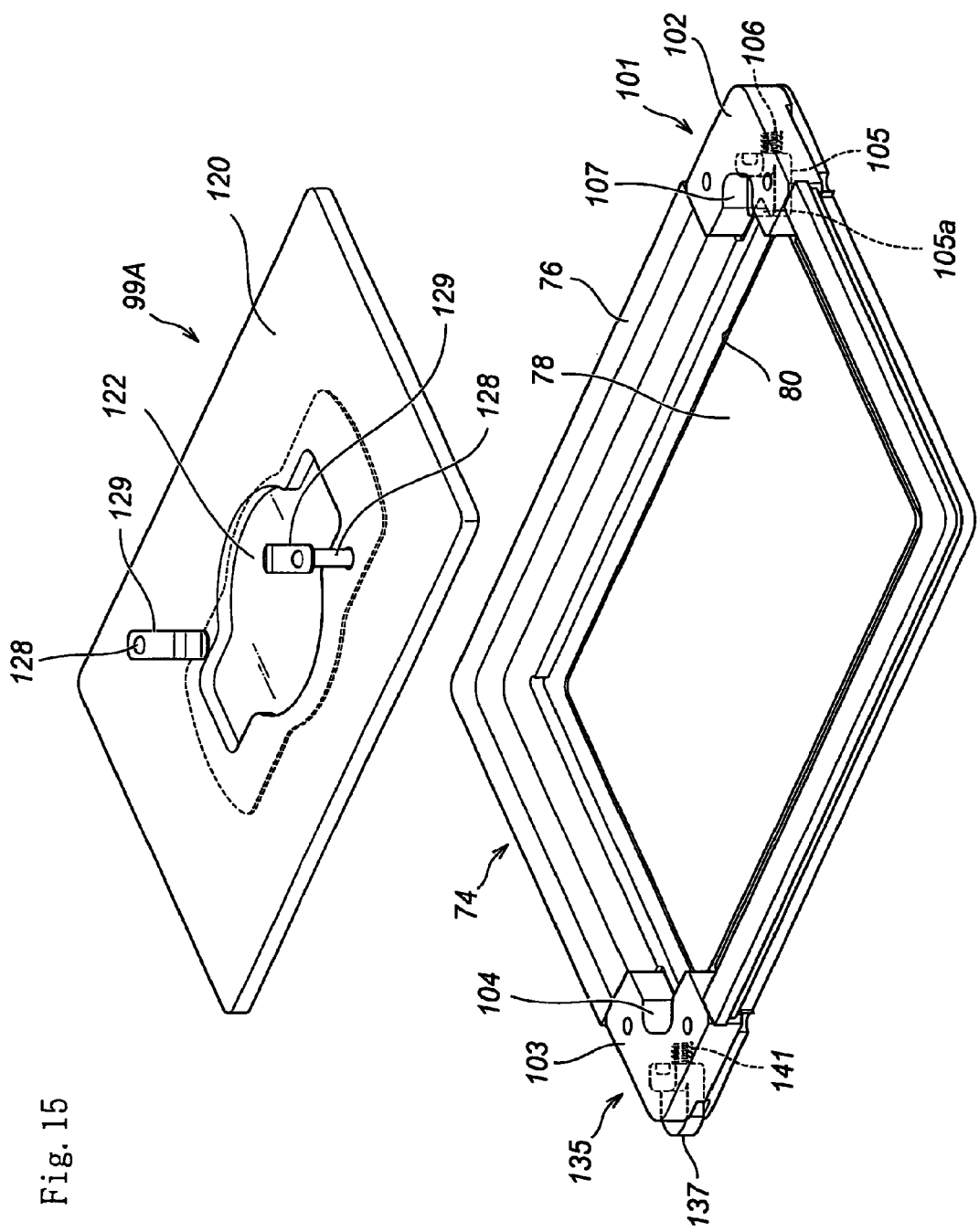
FIG. 15 is a perspective view illustrating the frame member and an adapter for a dish.
Figure 16:
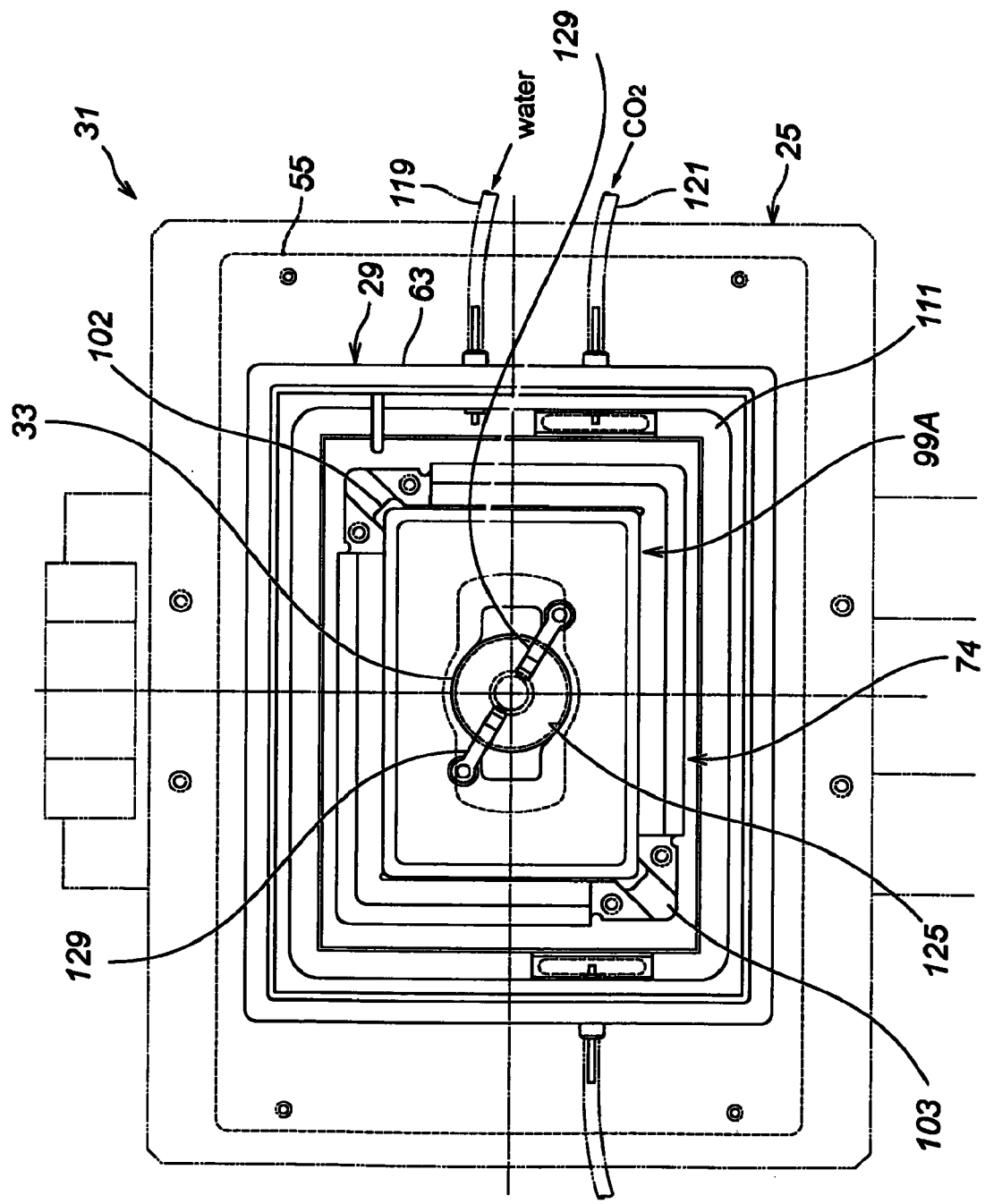
FIG. 16 is a plan view illustrating the microscope observing unit in which the culture device is set on the stage with the adapter for the dish of FIG. 15.

An adapter 99A for the dish 33 is shown in FIGS. 15 and 16.

The adapter 99A has a body 120 of a rectangular plate member of the same width and the same length as those of the well plate 37 or 39. The thickness of the body 120 is about 3 mm. At the central portion of the body 120 is formed an opening 122. The opening 122 has a circular portion of the size just to fit the body 33a of the dish 33 and rectangular portions extending in opposite x-directions from the circular portion. A pair of struts 128 extends from the body 120. A presser plate 129 is supported pivotally on the end of each strut 128.

Figure 17:
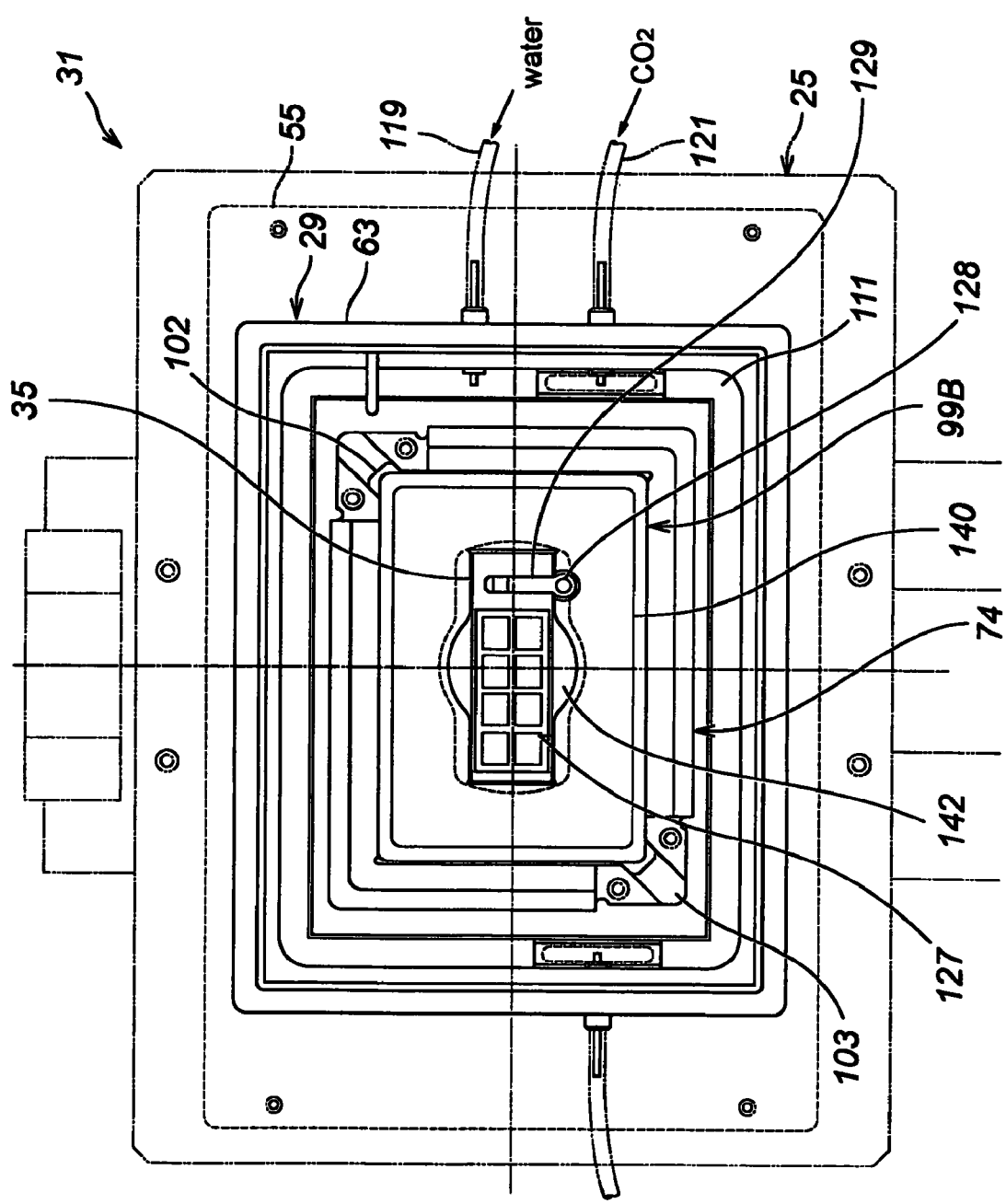
FIG. 17 is a plan view illustrating the microscope observing unit in which the culture device is set on the stage with the adapter for the well plate of FIG. 2(b)

An adapter 99B for the well plate 35 is shown in FIG. 17.

The adapter 99B has a body 140 of a rectangular plate member of the same width and the same length as those of the well plate 37 or 39. The thickness of the body 140 is about 3 mm. At the central portion of the body 140 is formed an opening 142. The opening 142 has a rectangular portion of the size just to fit the slide glass 35a of the well plate 35 and semi-circular portions extending in opposite y-directions from the rectangular portion. A strut 128 extends from the body 140. A presser piece 129 is supported pivotally on the end of strut 128.

Figure 18:
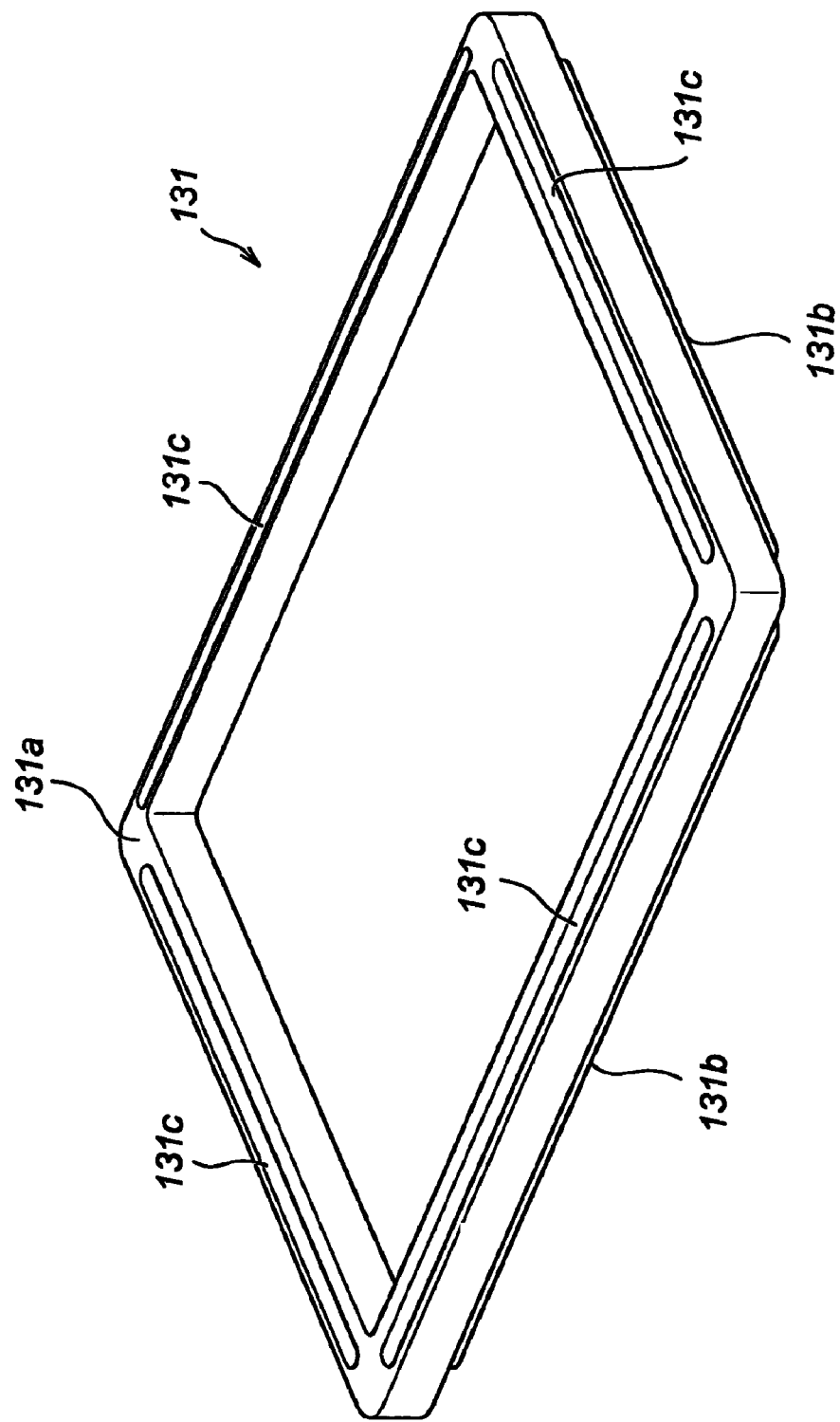
FIG. 18 is a perspective view illustrating a spacer.
Figure 19:
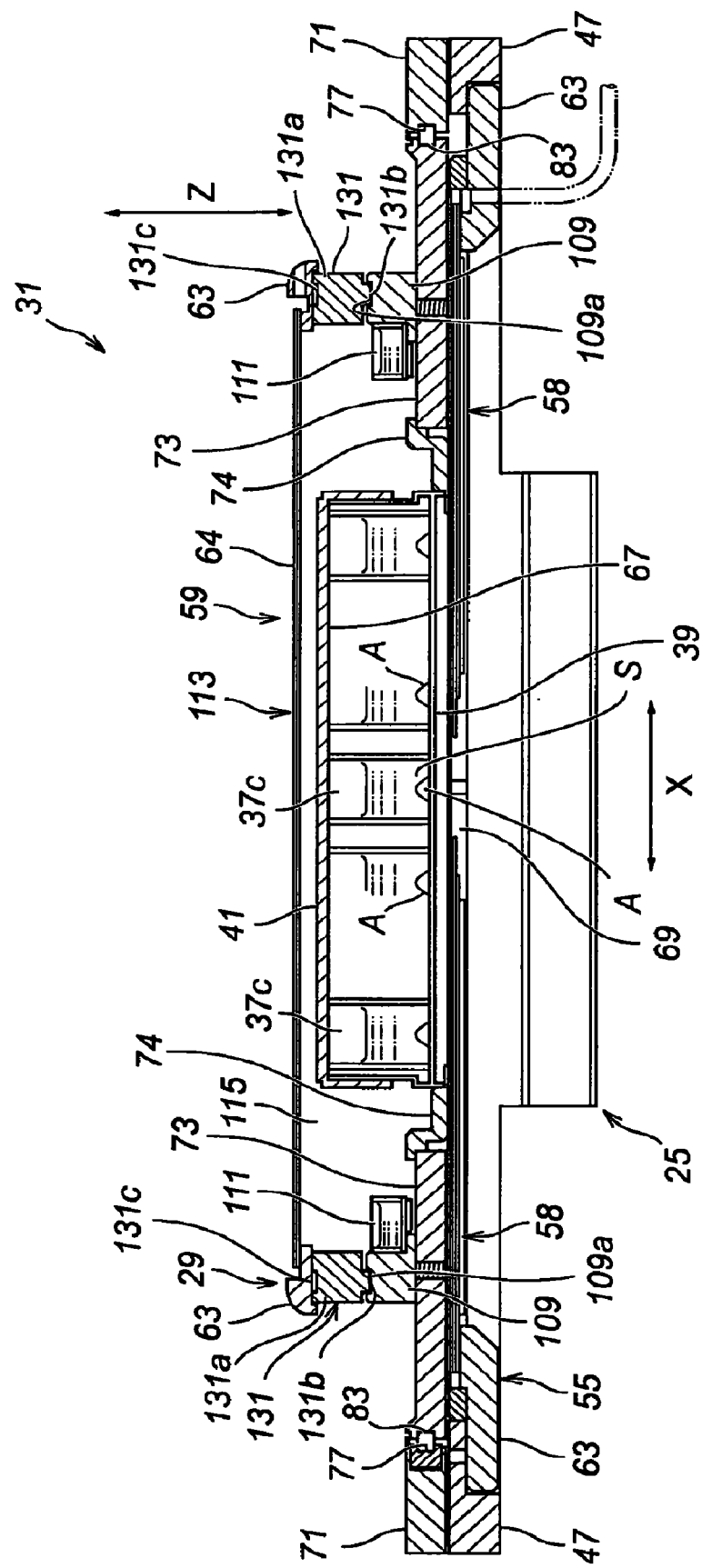
FIG. 19 is a cross-sectional view, corresponding to FIG. 9, illustrating the movable base in which the well plate of FIG. 2(d) is contained in the enclosed space, which has been enlarged in its height with the spacer of FIG. 18.

A spacer frame 131 is shown in FIGS. 18 and 19.

The spacer frame 131 is incorporated when a relatively higher culture vessel such as the well plate 39 is used.

A body 131a of the spacer frame 131 has a fitting protrusion 131b on the lower surface thereof and a fitting recess 131c on the upper surface thereof.

Using method of the microscope stage 25 and the microscope observing unit 31 will now be described in detail.

The fixing base 47 is secured to the body 7 of the microscope 1 by means of bolts B, whereby the microscope stage 25 is attached to the microscope 1. The vessel-keeping frame 74 is mounted in the opening 53. When mounting the vessel-keeping frame 74, the tongue 137 is being urged on the inner peripheral surface of the opening 53 against the coil spring 141 so that the frame 74 is be secured within the opening 53 without any play.

Subsequently, the well plate 37, each compartment 37c of which is filled with a culture solution S and cells A to be observed, is mounted within the opening 78 of the vessel-keeping frame 74 and disposed on the inwardly extending shelf shaped portion 80 of the frame member 76. When mounting the well plate 37, one corner portion of the body 37a is fit into the recessed portion 105a of the tongue 105 of the well plate fixing means 101 to urge the tongue 105 into the corner block 102. While keeping the condition, the body 37a of the well plate 37 is being fit into the opening 78. The corner of the body 37a abuts the cutout 107 of the corner block 102 and the opposite corner thereof is fit within the cutout 104 of the corner block 103. The body 37a is adapted to be urged onto the cutout 104 by means of the tongue 105 pushing the body 37a of the well plate 37. Thus, the well plate 37 is secured within the vessel-keeping frame 74 without any play.

The housing 109 of the culture device 29 is then disposed on the upper base 73. The housing 109 is adapted to be positioned to circumscribe the well plate 37. The top heater 113 is disposed on the housing 109 to make the enclosed space 115 defined by the upper base 73, the housing 109, and the top heater 113.

In order to increase the temperature of the enclosed space 115, the heating section 58 of the stage heater 55 and the transparent heater 64 of the top heater 113 are switched on. The heat energy produced by the heating section 58 and the transparent heater 64 is controlled based on information from temperature sensors (not shown) so as to keep the temperature in the enclosed space 115 at a predetermined value.

Water is supplied within the water tank 111 from the water supplying means (not shown) through the water supplying conduit 119 and the water supplying tube 112. The water is heated by the stage heater 55 and the top heater 113 and vaporized to achieve a predetermined humidity within the enclosed space 115.

The enclosed space 115 is further filled with $CO_2$ gas delivered from the $CO_2$ tank (not shown) through the gas supplying conduit 121 and the gas supplying tube 114.

Thus, the atmosphere within the enclosed space 115 in the temperature, the humidity, and the concentration of $CO_2$ is controlled to satisfy predetermined values, respectively.

When observing the cells A accommodated within the well plate 37, the movable base 49 are shifted in the x-direction and/or the y-direction by manipulating the control knobs 95 and/or 97. Thus, the cells A accommodated in the respective compartments 37c can be observed by shifting them to cross the optical axis L of the objective 5.

Figure 9:
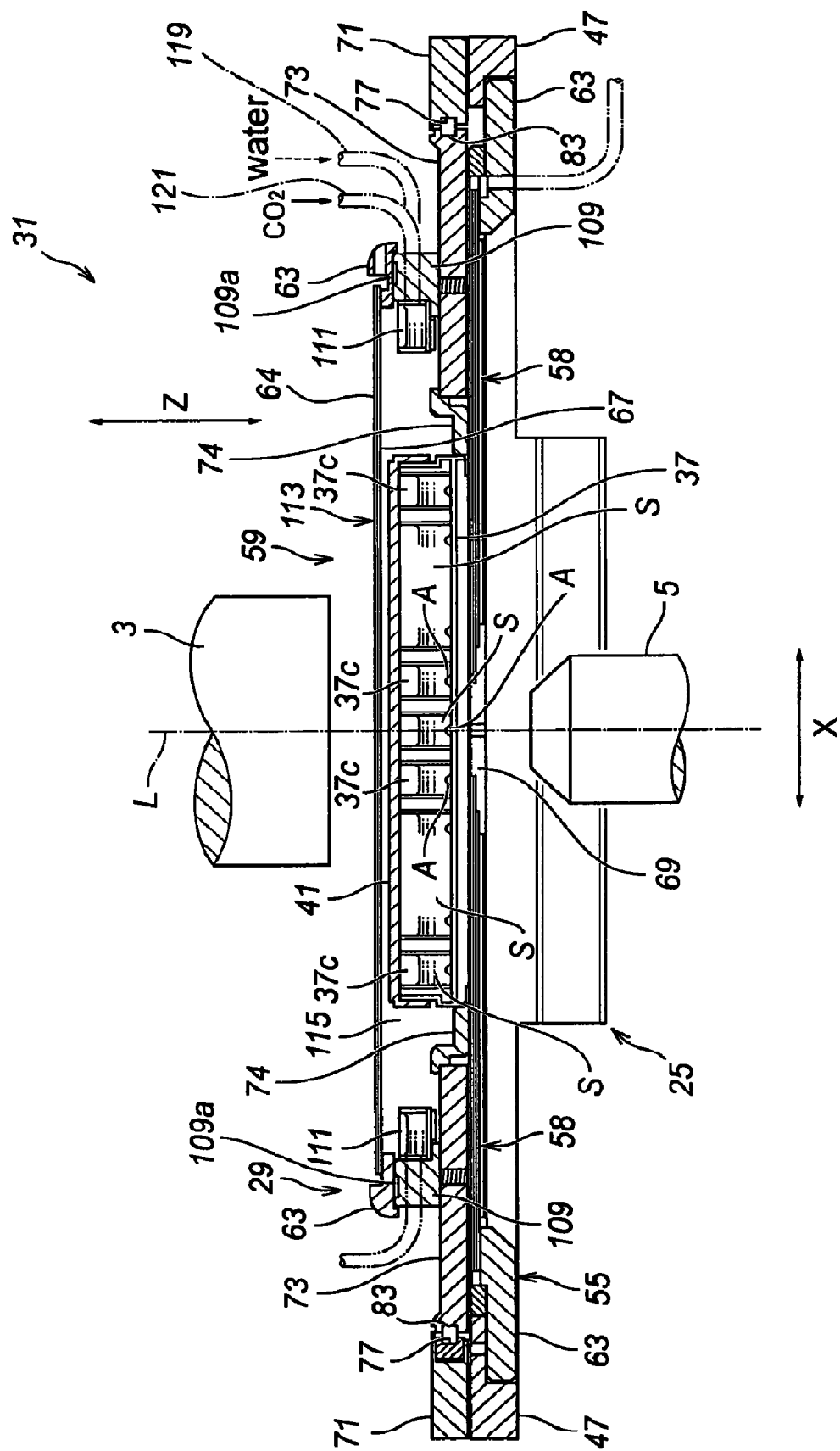
FIG. 9 is a cross-sectional view along the A-A line in FIG. 8.
Figure 10:
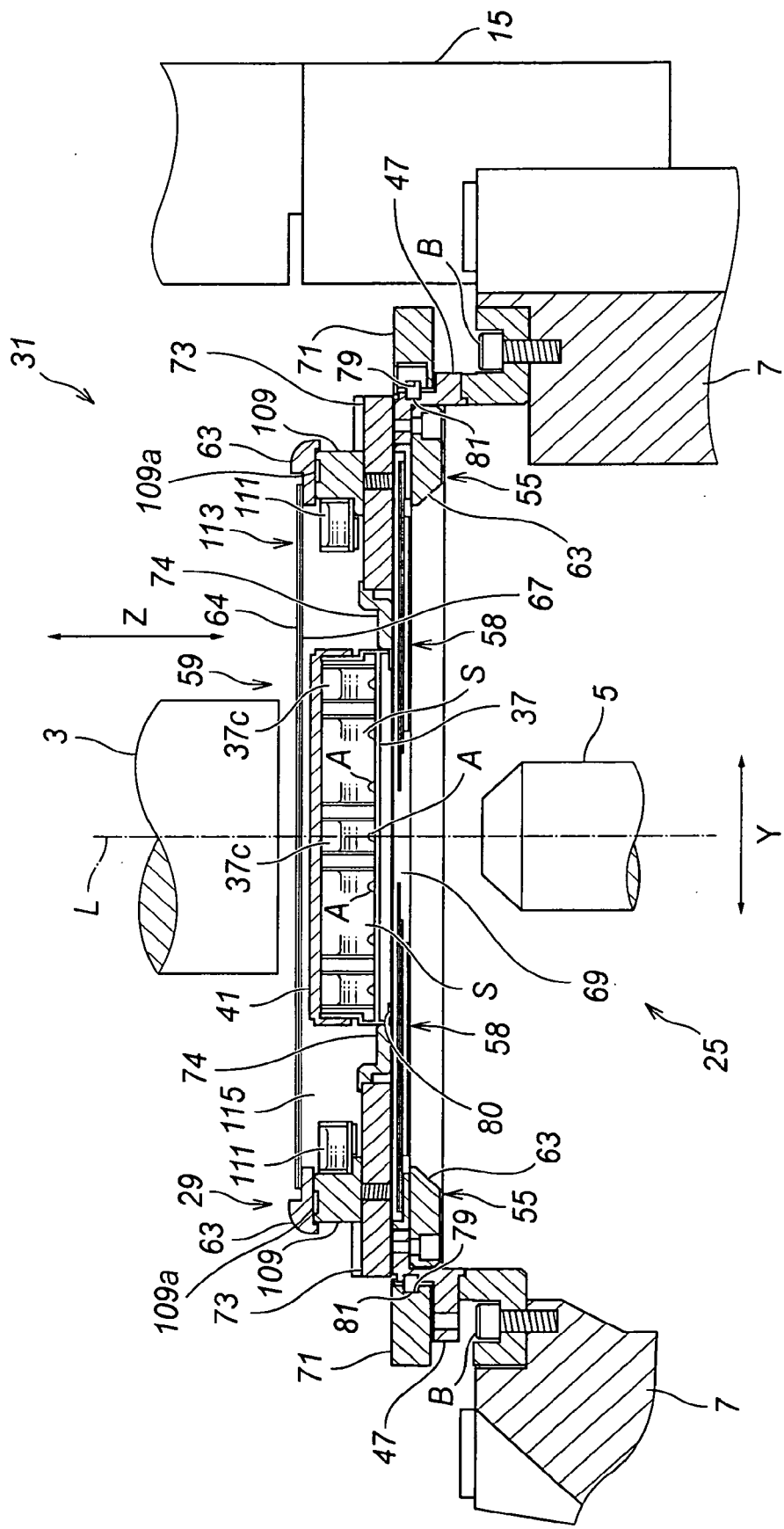
FIG. 10 is a cross-sectional view along the B-B line in FIG. 8.
Figure 11:
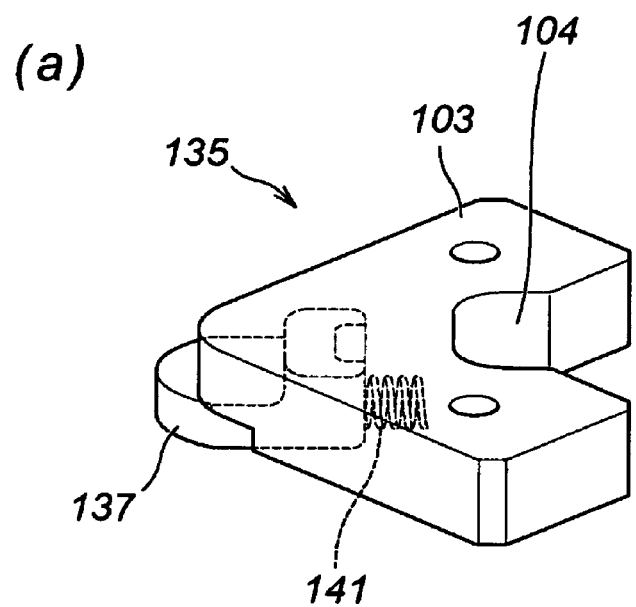
FIG. 11 is a perspective view illustrating a frame fixing means provided on a frame member.
Figure 11:
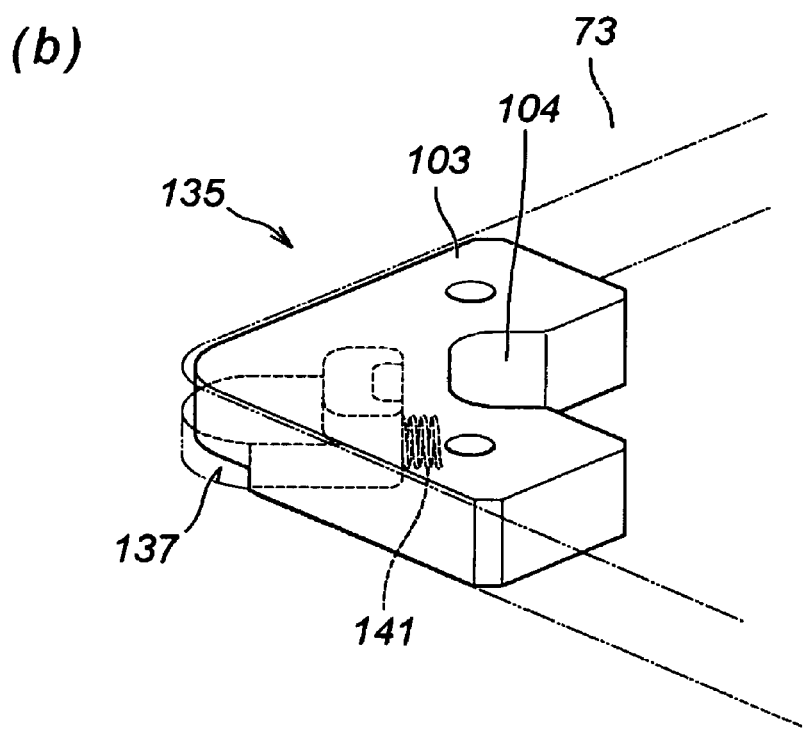
Figure 12:
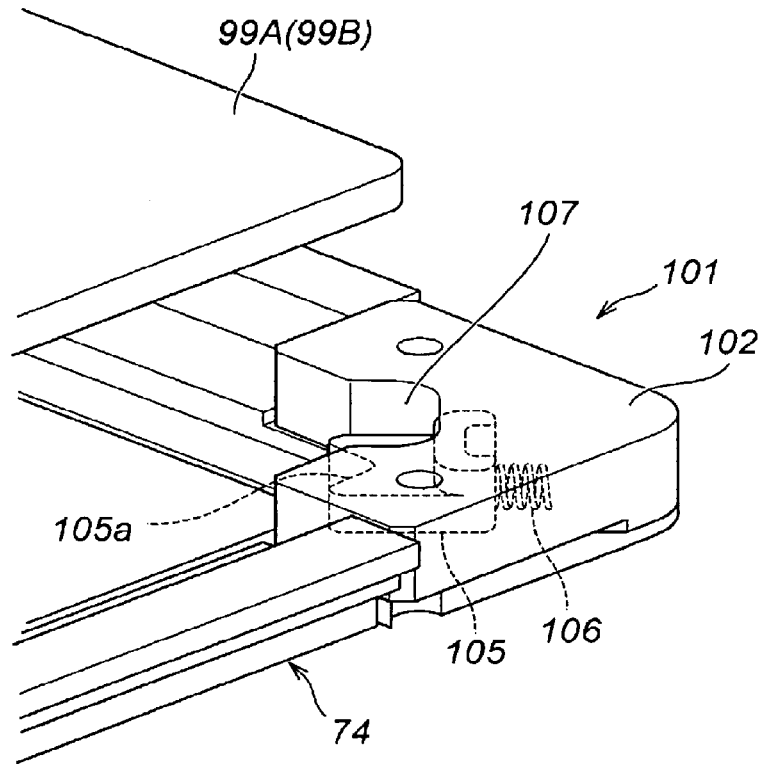
FIG. 12 is a perspective view illustrating a well plate fixing means provided on the frame member.
Figure 12:
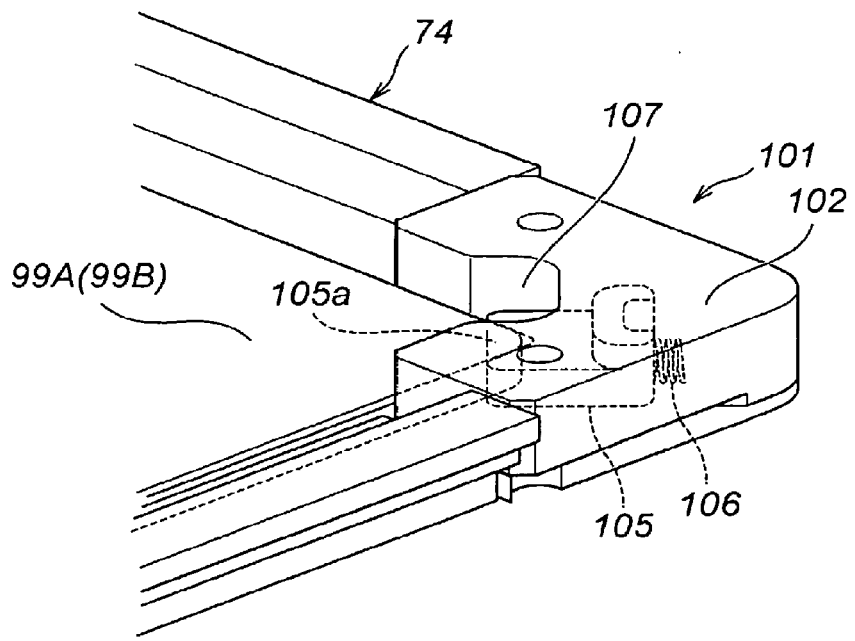
Figure 13:
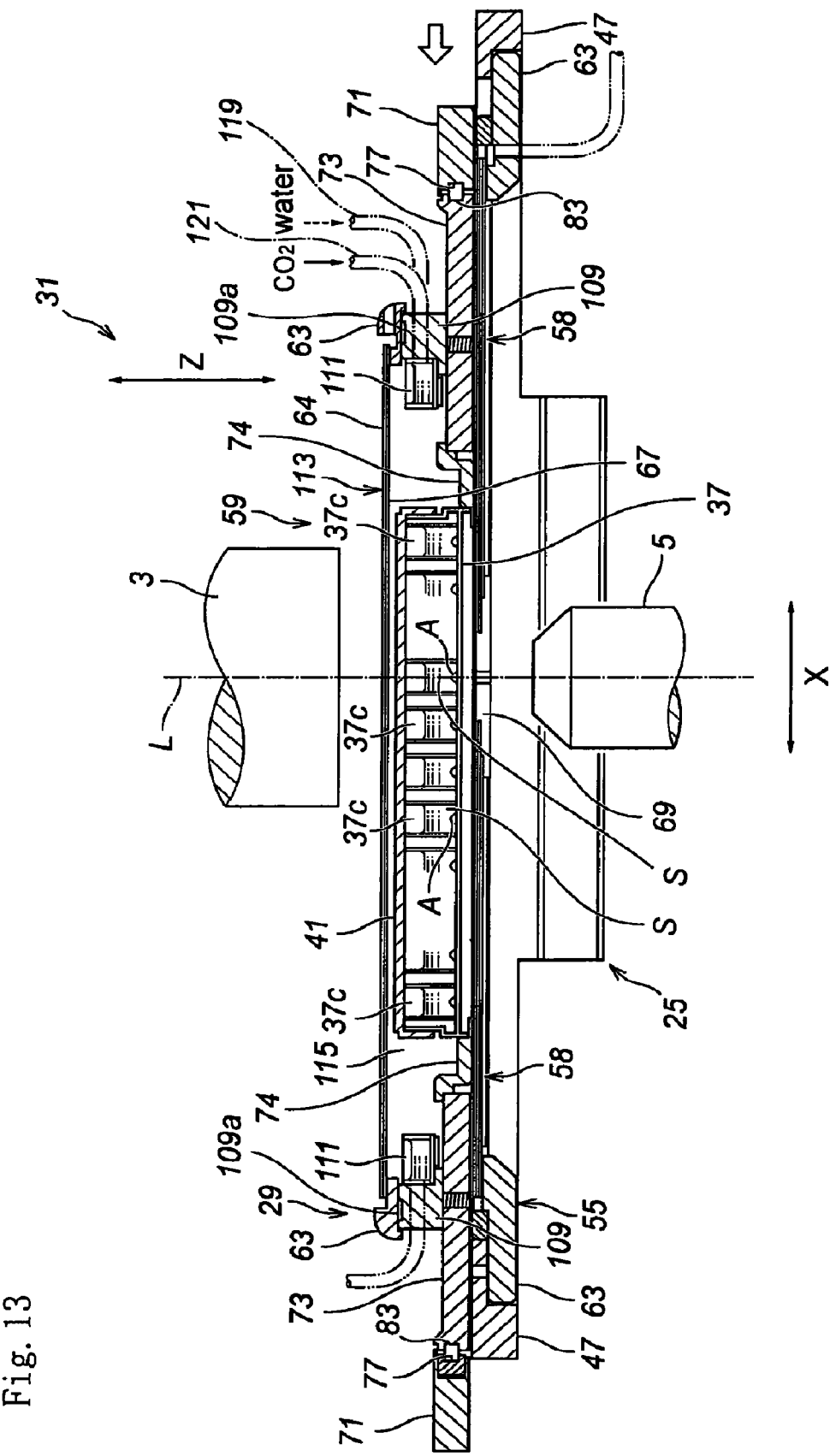
FIG. 13 is a cross-sectional view illustrating a movable base after being displaced from a position as shown in FIG. 9 in x-direction.
Figure 14:
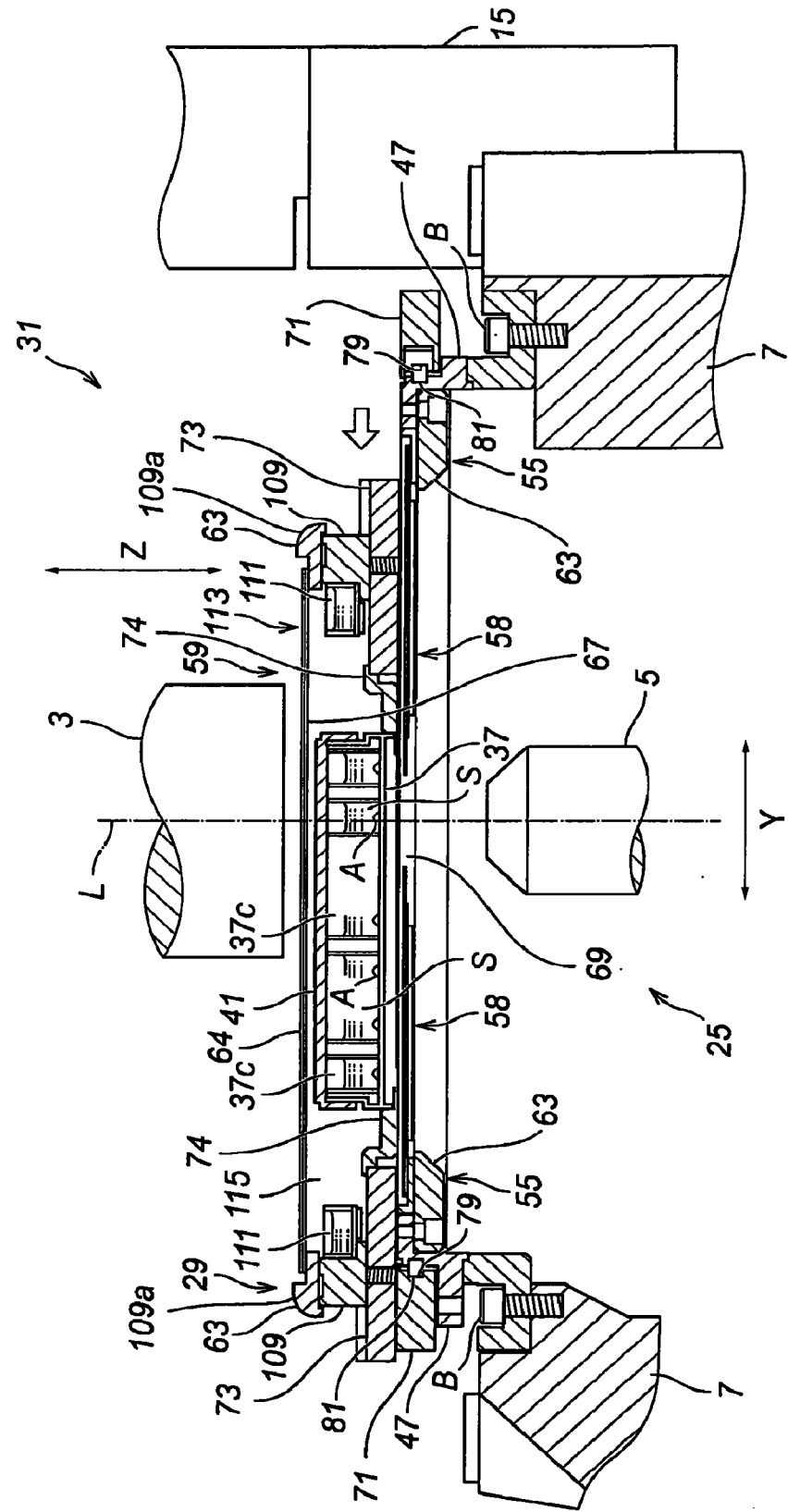
FIG. 14 is a cross-sectional view illustrating the drive base after being displaced from a position as shown in FIG. 10 in y-direction.

In other words, the lower base 71, together with the upper base 73, is shifted from the position as shown in FIG. 9 in the x-direction by turning the control knob 95 to rotate the pinion 92 to displace the rack 85. In this connection the well plate 37 disposed on the upper base 73 is also be shifted in the x-direction as shown in FIG. 13. The upper base 73 is shifted from the position as shown in FIG. 10 in the y-direction by turning the control knob 97 to rotate the pinion 94 to displace the rack 87. In this connection the well plate 37 disposed on the upper base 73 is also shifted in the y-direction as shown in FIG. 14.

All the cells A accommodated within compartments 37c of the well plate 37 is always warmed nevertheless of whether the movable base 49 is shifted in any positions such as in FIGS. 9, 13, 10, and 14, since the heating section 58 is of the size and the configuration sufficient to face with the well plate 37 disposed on the movable base 49.

The objectives 5 can bring closer to the cells A than in the case of the microscope stage of the prior art since the thickness of the microscope stage 25 of the present invention is reduced substantially relative to the stage of the prior art. In this connection, the objectives of high magnifying power can be focused on the cells A. In addition, the condenser 3 can also bring closer to the cells A. This will allow the condensation of the sufficient amount of light onto the cells A.

When it is intended to make observation by using the dish 33 as shown in FIGS. 15 and 16, the adapter 99A is attached to the vessel-keeping frame 74 in spite of the well plate 37. The adapter 99A is fit within the opening 78 and disposed on the inwardly extending shelf shaped portion 80 while urging the one corner portion of the adapter 99A with the tongue 105. The body 33a of the dish 33 filled with the cells A together with the culture solution, will then be fit within the opening 122 of the adapter 99A, and be secured thereto by pivoting the pair of presser pieces 129 and elasticity urging the lid 33b of the dish 33 with them.

The method for operating the movable base 49 and the method for making observation of the cells A are the same as those used in the case of the well plate 37.

When it is intended to make observation by using the well plate 35 as shown in FIG. 17, the adapter 99B is attached to the vessel-keeping frame 74 in the same way as is used in the case of adapter 99A. The well plate 35 is secured to the adapter 99B by fitting the well plate 35 into the opening 142 and pressing and elasticity urging the slide glass 35b with the presser pieces 129.

When it is intended to make observation by using the well plate 39 as shown in FIG. 19, the spacer frame 131 is interposed between the housing 109 and the top heater 113 with fitting the protrusion 131b formed on the lower surface of the spacer frame 131 into the recess 109a provided on the upper surface of the housing 109. Thus, unintentional displacement of the spacer frame 131 from the housing 109 will be avoided.

Further, the spacer frame 131 will provide an additional height to the enclosed space 115 for accommodating the well plate 39.

When it is intended to employ a culture vessel higher than the well plate 39, two or more spacer frames 131 can be stacked by fitting the protrusion 131b formed on the lower surface of the upper spacer frame 131 into the recess 131c formed on the upper surface of the lower one. Thus, unintentional displacement of the spacer frames 131 will be also avoided.

Although preferred embodiments of the present invention have been described, those of skill in the art will appreciate the variation and modification may be made without departing from the spirit and scope thereof as defined by appended claims.

For example, a microscope to which the microscope stage of the present invention is to be applied may not be limited to the inverted microscope 1. The microscope stage of the present invention may also be applied to stereo microscopes and upright microscopes in which an objective is positioned above objects such as the cells A and a condenser is positioned below the cells A.

Light transmitting portion formed through the movable base 49 and formed through the stage heater 55 are not necessarily the opening 53 and the opening 69, namely thought hole with no material, but also any transparent material such as a transparent glass plate may be used to cover the apertures. In the latter case, the transparent glass plate can be made of a transparent heater of the same structure as that of the top heater 113. In other words, the heating section 58 of the stage heater 55 may be formed by such transparent heater.

As discussed hereinabove, the shape and the size of the opening 53 formed through the movable base 49, the opening 78 of the vessel-keeping frame 74, and the heating section 58 of the stage heater 55 is determined on the basis of the shape and the size of the well plates 37 and 39. If it is intended to use a culture vessel of size larger than those of the well plates 37 and 39, the shape and the size of the opening of the components of the microscope stage may be designed or determined on the basis of the shape and the size of the culture vessel.

Of course, the shape and the size of the adapters may be modified in dependent on the shape and the size of a culture vessel to be used.

The means for shifting or driving the movable base 49 is not limited to the control knobs 95 and 97. The movable base 49 may be operated by servo or stepper motors. Further, ball and nut mechanism may be used instead of the rack and pinion mechanism.

The invention claimed is:

1. A microscope stage comprising:
   a fixed base,
   a movable base on which a culture vessel accommodating an object to be observed is disposable, the movable base being movable relative to the fixed base in two-dimensional directions within a plane extending perpendicular to an optical axis of an objective lens,
   a shift means for shifting the movable base in the two-dimensional directions,
   a light-transmittable portion for passing light, formed through the movable base with a size corresponding to an object-accommodating portion in the culture vessel,
   a stage heater provided on the fixed base for heating the entire culture vessel regardless of a two-dimensional displacement of the movable base, and
   a light-transmittable, circular portion of the stage heater for passing the light therethrough for making observation through the objective lens.

2. The microscope stage according to claim 1, wherein the circular portion of the stage heater for passing the light is provided opposite to a condenser of a microscope.

3. The microscope stage according to claim 1, wherein the light-transmittable portion of the movable base is an opening.

4. The microscope stage according to claim 3, wherein the size of an opening of the movable base corresponds to a two-dimensional maximum size of the culture vessel.

5. The microscope stage according to claim 4, further comprising an adapter adaptable within the opening of the movable base, the adapter being formed with an opening of a size corresponding to another small culture vessel.

6. The microscope stage according to claim 5, wherein the movable base includes a fixing means for securing the culture vessel of maximum size or the adapter in the opening of the movable base.

7. The microscope stage according to claim 1, wherein the light-transmittable, circular portion of the stage heater is a through hole.

8. The microscope stage according to claim 1, wherein a heating section of the stage heater includes a transparent base plate and an electrically conductive transparent film.

9. The microscope stage according to claim 1, wherein
the movable base includes a lower base and an upper base,
the lower base is linearly movable relative to the fixed base in a first direction, and
the upper base is linearly movable relative to the lower base in a second direction perpendicular to the first direction.

10. The microscope stage according to claim 9, wherein the upper surface of the lower base is recessed to receive the upper base, and the lower surface of the lower base is recessed to receive the fixed base.

11. A microscope observing unit including;
the microscope stage according to claim 1,
a culture device disposed on the movable base to form an enclosed space in combination with the movable base, provided with a means for controlling the atmosphere of the enclosed space in temperature and humidity.

12. The microscope observing unit according to claim 11, the culture device comprising:
a housing adapted to be disposed on the movable base, and
a top heater adapted to be disposed on the housing,
wherein the top heater is provided with a heat producing portion covering over an upper opening of the housing, with a transparent base plate and an electrically conductive transparent film formed thereon.

13. The microscope observing unit according to claim 12, further comprising a spacer frame adapted to be interposed between the top heater and the housing for providing an additional height to the enclosed space in correspondence to the height of the culture vessel being used.

* * * * *